United States Patent
Boström

(10) Patent No.: US 10,589,033 B2
(45) Date of Patent: Mar. 17, 2020

(54) MEDICAMENT DELIVERY DEVICE

(71) Applicant: CAREBAY EUROPE LTD, Sliema (MT)

(72) Inventor: Anders Boström, Solna (SE)

(73) Assignee: SHL MEDICAL AG, Zug (CH)

( * ) Notice: Subject to any disclaimer, the term of this patent is extended or adjusted under 35 U.S.C. 154(b) by 223 days.

(21) Appl. No.: 15/748,970

(22) PCT Filed: Jul. 6, 2016

(86) PCT No.: PCT/EP2016/065941
§ 371 (c)(1),
(2) Date: Jan. 30, 2018

(87) PCT Pub. No.: WO2017/029021
PCT Pub. Date: Feb. 23, 2017

(65) Prior Publication Data
US 2019/0009036 A1 Jan. 10, 2019

(30) Foreign Application Priority Data
Aug. 19, 2015 (SE) ...................... 1551079

(51) Int. Cl.
*A61M 5/315* (2006.01)
*A61M 5/24* (2006.01)

(52) U.S. Cl.
CPC .... *A61M 5/31585* (2013.01); *A61M 5/31575* (2013.01); *A61M 5/31593* (2013.01); *A61M 5/24* (2013.01); *A61M 5/3158* (2013.01)

(58) Field of Classification Search
CPC .... A61M 5/178; A61M 5/2422; A61M 5/315; A61M 5/31; A61M 5/31565;

(Continued)

(56) References Cited

U.S. PATENT DOCUMENTS

2006/0178630 A1* 8/2006 Bostrom ............. A61M 5/2066
604/135
2012/0253287 A1* 10/2012 Giambattista ..... A61M 5/31553
604/189

(Continued)

FOREIGN PATENT DOCUMENTS

| EP | 1843808 B1 | 9/2010 |
| WO | 2011/081867 A2 | 7/2011 |
| WO | 2015/032778 A1 | 3/2015 |

OTHER PUBLICATIONS

International Search Report and Written Opinion for PCT Pub. No. PCT/EP2016/065941, completed Sep. 23, 2016.

*Primary Examiner* — Jason E Flick
(74) *Attorney, Agent, or Firm* — McDonnell Boehnen Hulbert & Berghoff LLP

(57) ABSTRACT

A medicament delivery device is presented having a body, an axially biased plunger rod provided with a first external thread, an activation member arranged to activate the plunger rod, a tubular medicament scale member receiving the activation member, which tubular medicament scale member is rotatable relative to the body and provided with a visual medicament dose scale, a stop nut that receives the plunger rod, where the stop nut is provided with an internal thread engaging with the first external thread of the plunger rod, and a gear train arrangement. The gear train arrangement couples the stop nut to the tubular medicament scale member for transferring rotational motion of the stop nut to the tubular medicament scale member to convey a measure of axial movement of the plunger rod to provide an indication, on the visual medicament dose scale, of an amount of expelled medicament.

20 Claims, 6 Drawing Sheets

(58) Field of Classification Search
CPC .......... A61M 5/31566; A61M 5/31573; A61M 5/31576; A61M 5/31578; A61M 5/31583; A61M 5/3159; A61M 5/24; A61M 5/31575; A61M 5/3158; A61M 5/31585; A61M 5/31593
USPC ........................................................ 604/211
See application file for complete search history.

(56) References Cited

U.S. PATENT DOCUMENTS

2015/0133869 A1* 5/2015 Streit ................ A61M 5/31585
604/189
2016/0271332 A1* 9/2016 Bilton .................... A61M 5/20

\* cited by examiner

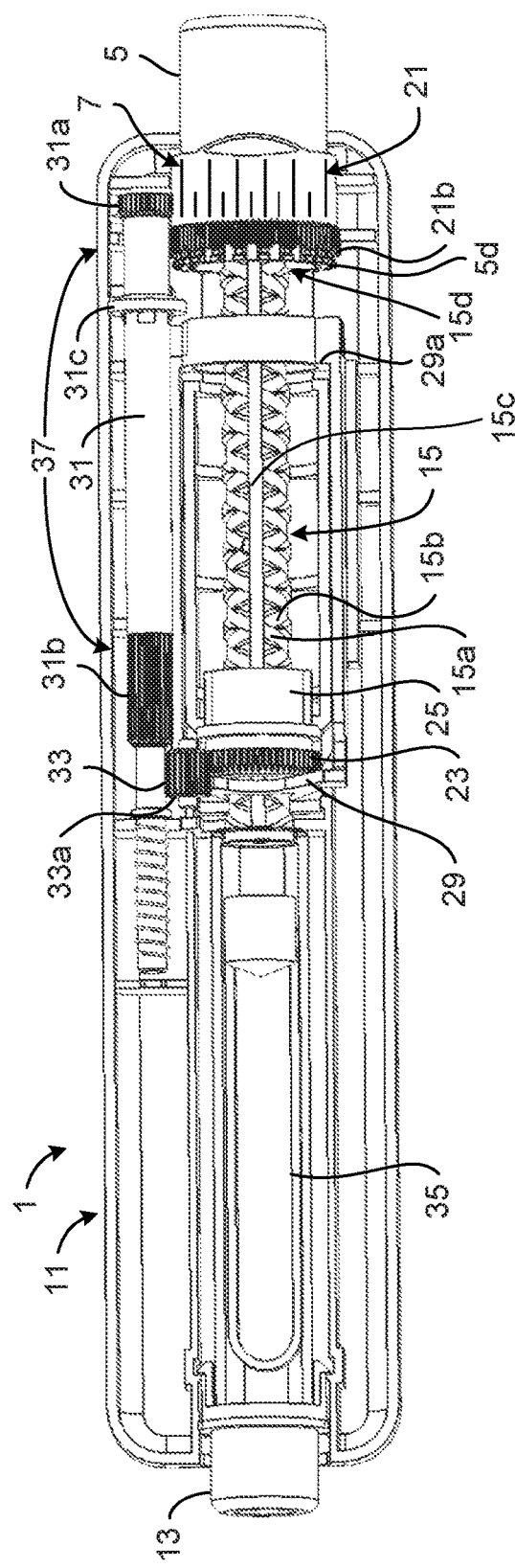
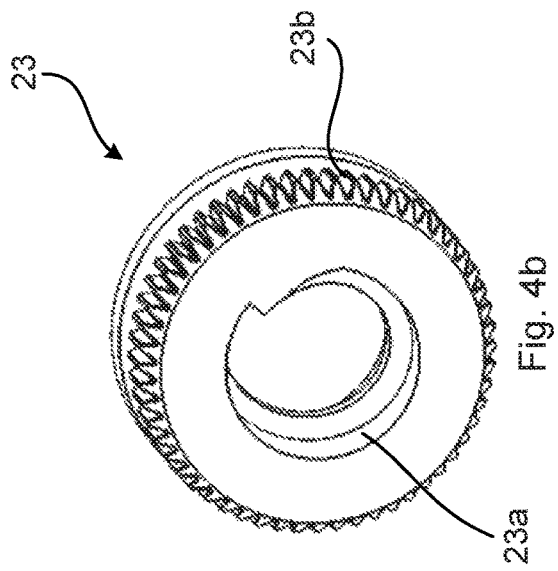
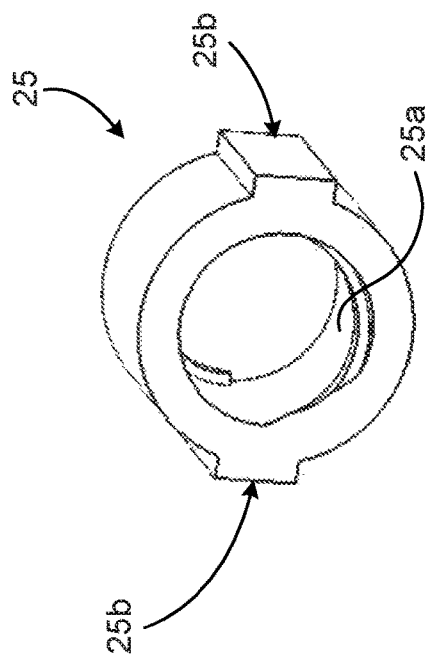
Fig. 3
Fig. 4a
Fig. 4b

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/065941 filed Jul. 6, 2016, which claims priority to Swedish Patent Application No. 1551079-5 filed Aug. 19, 2015. The entire disclosure contents of these applications are herewith incorporated by reference into the present application.

TECHNICAL FIELD

The present disclosure generally relates to a medical device and in particular to a medicament delivery device for administration of a medicament to a patient.

BACKGROUND

Medicament delivery devices such as auto-injectors and inhalers nowadays provide possibilities for the users themselves to handle medicament delivery in an easy, safe and reliable manner. Moreover, such devices also facilitate the administration of drugs for hospital personnel.

A number of functions for medicament delivery devices have been developed such as controlled injection rate and multiple doses with means for varying the quantity of each dose.

EP1843808 B1 discloses a device for delivering a medicament which has the capability to adjust the dose. In particular, EP1843808 B1 discloses an injection device comprising a longitudinally movable piston and a spring arrangement acting on the piston and capable of exerting a force on the components, a first holding means arranged and capable of holding the piston in a force-loaded state, and an activator means capable of acting on the first holding means for releasing the piston. The dose can be set by turning a dose setting knob, so that a dose quantity indication for the chosen dose, on the outside of the main upper housing, is in register with an indication mark on the knob. The turning of the knob causes the dose setting sleeve also to turn. The turning of the knob and the dose setting sleeve causes a rear nut to turn because the rear nut has ledges positioned in a groove of the sleeve. Turning of the knob and thus the dose setting sleeve furthermore causes the rear nut to move along the piston due to its threads being in engagement with the threads of the piston. This creates a distance between the rear nut and a front nut and sets the axial distance that the piston can move during medicament delivery. The dose can thereby be set.

SUMMARY

Although the above-described device provides means for setting a dose, it does not provide means for determining the amount of medicament that has been delivered during the course of administration in a simple manner.

In view of the above, a general object of the present disclosure is to provide a medicament delivery device which shows how much of a set dose has been delivered during drug administration.

There is hence provided a medicament delivery device comprising a body, an axially biased plunger rod provided with a first external thread, an activation member arranged to activate the plunger rod, a tubular medicament scale member receiving the activation member, which tubular medicament scale member is rotatable relative to the body and provided with a visual medicament dose scale, a stop nut which receives the plunger rod and which stop nut is provided with an internal thread engaging with the first external thread of the plunger rod, and a gear train arrangement arranged to, in a decoupled state decouple the stop nut from the tubular medicament scale member, and in a coupled state couple the stop nut to the tubular medicament scale member for transferring rotational motion of the stop nut to the tubular medicament scale member, in order to convey a measure of axial movement of the plunger rod to the tubular medicament scale member, thereby providing an indication, on the visual medicament dose scale, of an amount of expelled medicament.

By conveying a measure of the axial movement of the plunger rod to the tubular medicament scale member the amount of expelled medicament/the amount of remaining dose may be indicated on the visual medicament dose scale. A user may thereby at each instance during medicament administration determine the volume of medicament that has been expelled. As a result the user may administer a multiple number of doses with one charge of medicament i.e. one medicament container e.g. a cartridge. By means of the knowledge of the amount of medicament left, the content of the medicament container provided in the medicament delivery device may be subdivided into several doses that may be administered at different occasions. A multi-dose medicament delivery device may thus be provided.

Furthermore, if the medicament remaining in the container when the last dose is set is smaller than the set dose, the user may, after administration, determine the complementary amount that needs to be administered from the next container to get a complete dose.

The gear train arrangement is designed such that axial displacement of the plunger rod during medicament administration is translated into a rotation of the tubular medicament scale member, and in particular of the visual medicament dose scale, which corresponds to the volume of medicament expelled from the medicament delivery device.

According to one embodiment the gear train arrangement includes a scale rotation axle arranged parallel to the plunger rod, wherein the scale rotation axle is arranged to transfer rotational motion of the stop nut to the tubular medicament scale member.

According to one embodiment the scale rotation axle has a plurality of first scale rotation axle teeth engageable with scale member teeth of the tubular medicament scale member.

According to one embodiment the gear train arrangement comprises an intermediate wheel having intermediate wheel teeth engaging with stop nut teeth of the stop nut.

According to one embodiment the scale rotation axle has a plurality of second scale rotation axle teeth engageable with the intermediate wheel teeth of the intermediate wheel.

According to one embodiment the activation member is arranged to axially displace the scale rotation axle to enable the coupling between the stop nut and the tubular medicament dose scale member.

One embodiment comprises a dose setting tube receiving the plunger rod, wherein the dose setting tube is rotatably fixed to the activation member to prevent relative rotation between the dose setting tube and the activation member.

One embodiment comprises a dose setting nut receiving the plunger rod inside the dose setting tube, which dose setting nut is arranged between the stop nut and a distal end wall of the dose setting tube, wherein the internal thread of the stop nut is threaded in a first direction and the dose setting nut is provided with an internal thread threaded in a second direction, which plunger rod has a second external thread and wherein the internal thread of the dose setting nut engages with the second external thread of the plunger rod, and which dose setting nut is rotatably fixed relative to the dose setting tube.

According to one embodiment the first external thread and the second external thread of the plunger rod define double helix threads.

One embodiment comprises a lock member which in a first state, corresponding to the decoupled state of the gear train arrangement, is arranged to prevent rotation of the stop nut relative to the plunger rod and in a second state, corresponding to the coupled state of the gear train arrangement, is arranged to enable rotation of the stop nut relative to the plunger rod.

According to one embodiment the activation member is arranged to actuate the lock member from the first state to the second state.

According to one embodiment the plunger rod is rotatably fixed relative to the body.

According to one embodiment the activation member is movable between a start position and an end position, wherein the activation member is rotatably fixedly engaged with the tubular medicament scale member in the start position.

According to one embodiment the activation member is released from rotatably fixed engagement with the tubular medicament scale member in the end position.

According to one embodiment in the start position rotation of the activation member provides rotation of the dose setting nut and of the dose setting tube relative to the plunger rod, thereby setting an axial distance between the stop nut and the dose setting nut, wherein the amount of rotation of the activation member provides a measure of a medicament dose amount indicated on the visual medicament dose scale.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 3 is a side view of the medicament delivery device in FIG. 2, with one half of the body or housing and a dose setting tube removed;

FIG. 4a is a perspective view of an example of a dose setting nut;

FIG. 4b is a perspective view of an example of a stop nut;

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The medicament delivery device disclosed herein provides a multi-dose injection functionality by providing a visual indication of the amount of medicament that has been delivered to a user. The medicament delivery device comprises a body, a plunger rod, which when actuated expels medicament from a medicament container contained in the medicament delivery device, and a tubular medicament scale member provided with a visual medicament dose scale. The visual medicament dose scale is a visual scale provided along the periphery of the tubular medicament scale member. In order to provide a visual indication of the amount of medicament that remains in the medicament container at any given time when drug delivery has commenced the medicament delivery device comprises a gear train arrangement which mechanically provides a feedback of the linear or axial movement of the plunger rod during medicament delivery to the tubular medicament scale member. The gear train arrangement translates the linear movement of the plunger rod to a rotational motion of the tubular medicament scale member. The visual medicament dose scale is thereby rotated relative to the body. As the rotation of the tubular medicament scale member corresponds to the axial displacement of the plunger rod, the remaining amount of medicament is visually indicated by the visual medicament dose scale. An indication of the expelled dose amount may thus be provided. A pointer or indicator which is fixed relative to the visual medicament dose scale, for example provided on the body, enables reading any change of the visual medicament dose scale relative to the fixed pointer or indicator.

An example of a medicament delivery device will now be described in more detail with reference to FIGS. 1a to 8.

Figure 1A:
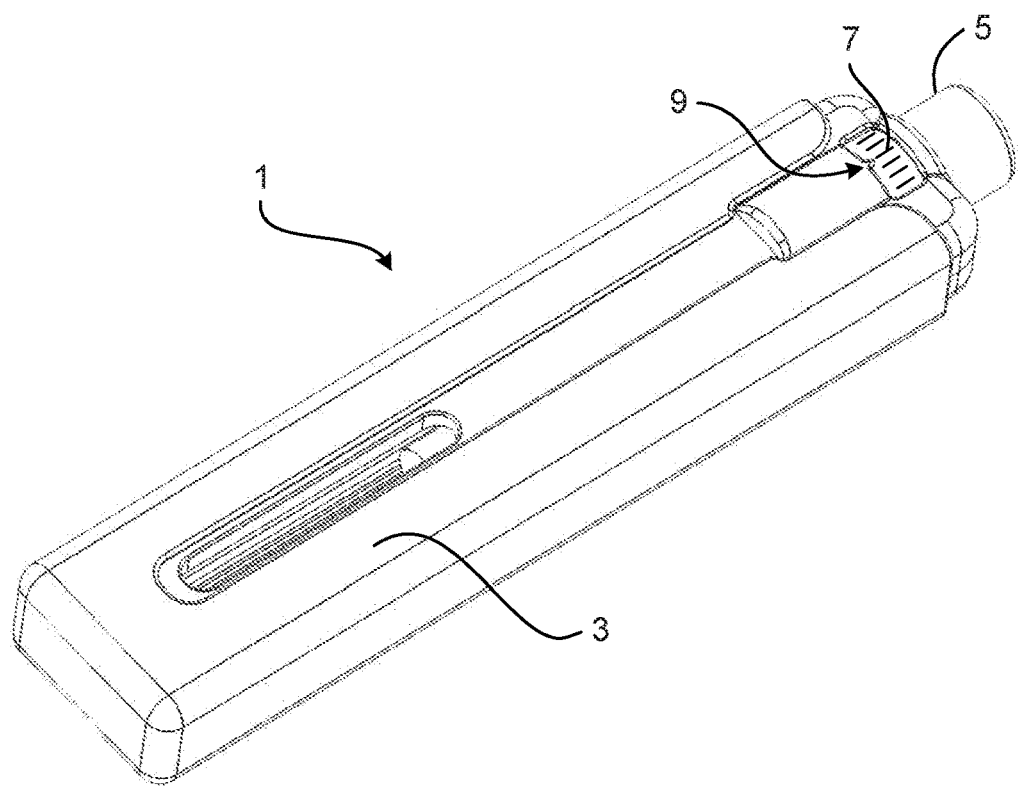
FIG. 1a is a perspective view of an example of a medicament delivery device including a cover.

FIG. 1a depicts a perspective view of an example of a medicament delivery device 1. The medicament delivery device 1 has a removable cover 3, an activation member 5, a visual medicament dose scale 7, and a pointer or indicator 9. The cover 3 is removed prior to use of the medicament delivery device 1.

Figure 1B:
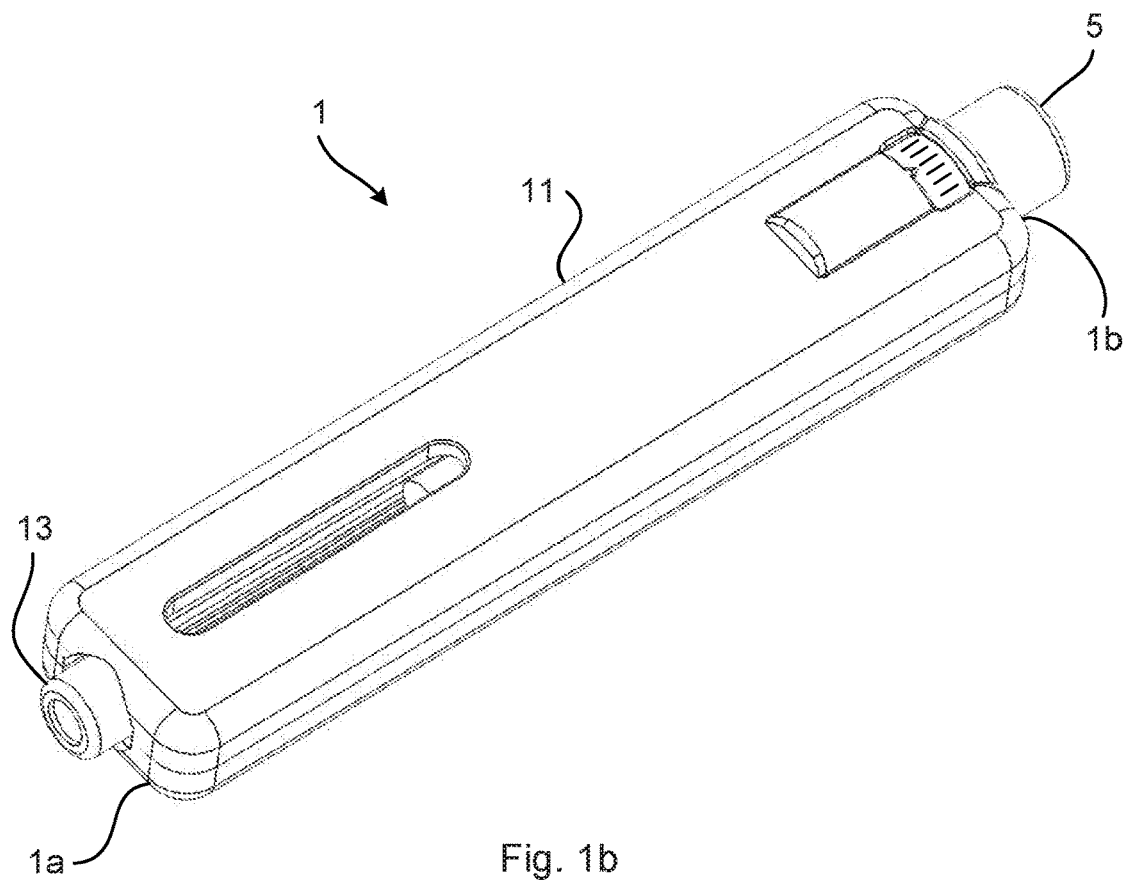
FIG. 1b is a perspective view of the medicament delivery device in FIG. 1a without the cover.

FIG. 1b shows a perspective view of the medicament delivery device 1 with the cover 3 removed. The medicament delivery device 1 has a proximal end 1a and a distal end 1b, and furthermore comprises a body 11, which forms a housing of the medicament delivery device 1. The body 11 may comprise a first half 11a and a second half 11b which are separable lengthwise. The medicament delivery device 1 also includes a cartridge retainer 13 to which a needle hub may be attached. The proximal end 1a is that end of the medicament delivery device 1 at which the cartridge retainer 13 is arranged and the distal end 1b is the opposite end, i.e. the end where the activation member 5 is located.

Figure 2:
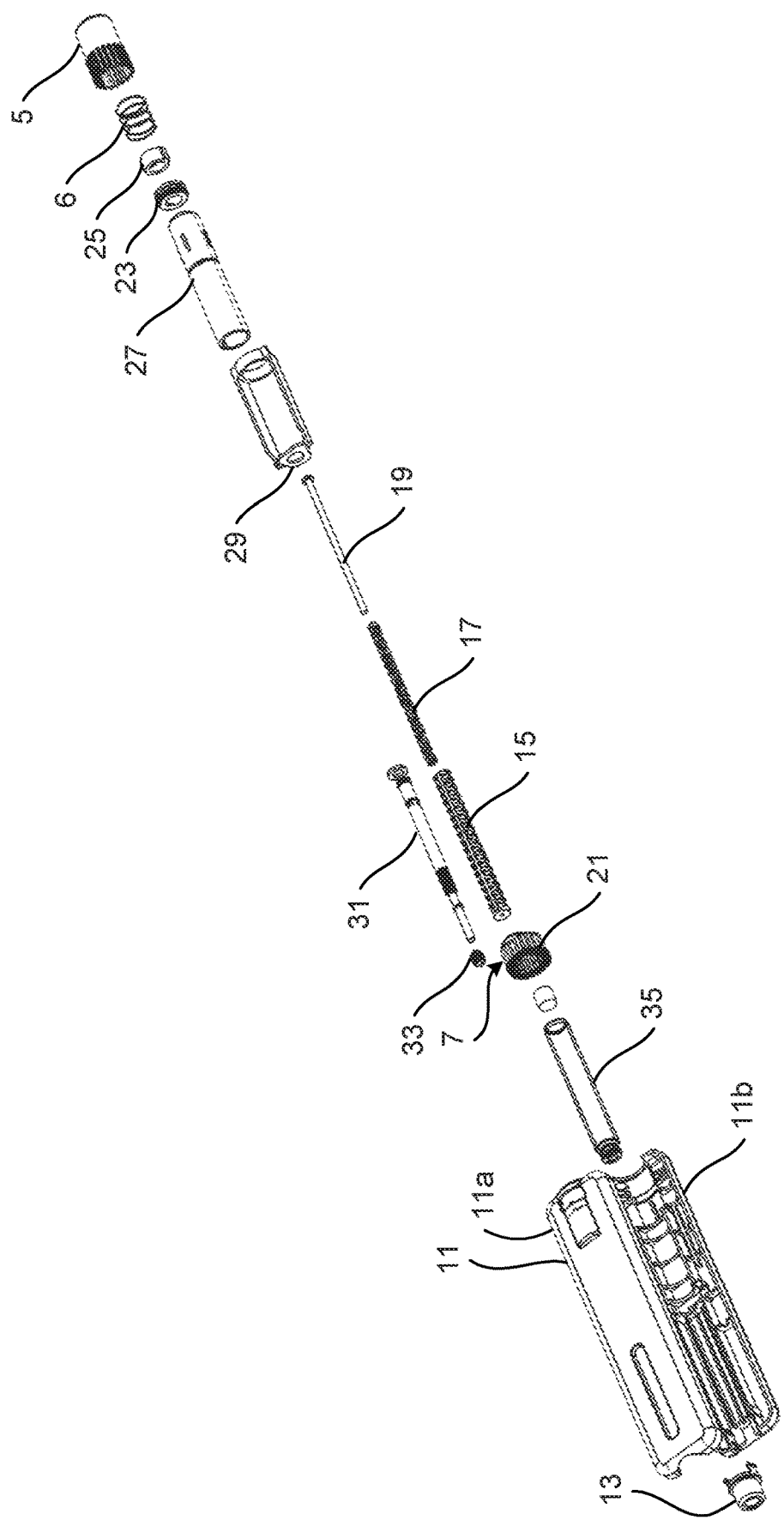
FIG. 2 is an exploded view of the medicament delivery device shown in FIG. 1b.

FIG. 2 shows an exploded view of the exemplified medicament delivery device 1, in which a number of components thereof are exposed. The medicament delivery device 1 further comprises a plunger rod 15, a first biasing member 17, for example a pre-tensioned spring, arranged to axially bias the plunger rod 15, a guide rod 19 arranged to support and to guide the first biasing member 17, a second biasing member 6, for example a spring, arranged to axially bias the activation member 5 towards a start position of the activation member 5, a tubular medicament scale member 21, the visual medicament dose scale 7 provided on the tubular medicament scale member 21, a stop nut 23, a dose setting nut 25, a dose setting tube 27, a lock member 29, a scale rotation axle 31, and an intermediate wheel 33. The stop nut 23, the intermediate wheel 33, the scale rotation axle 31 and the tubular medicament scale member 21 form a gear train arrangement 37, shown in FIG. 3. The medicament delivery device 1 may also comprise a medicament container 35.

Figure 6:
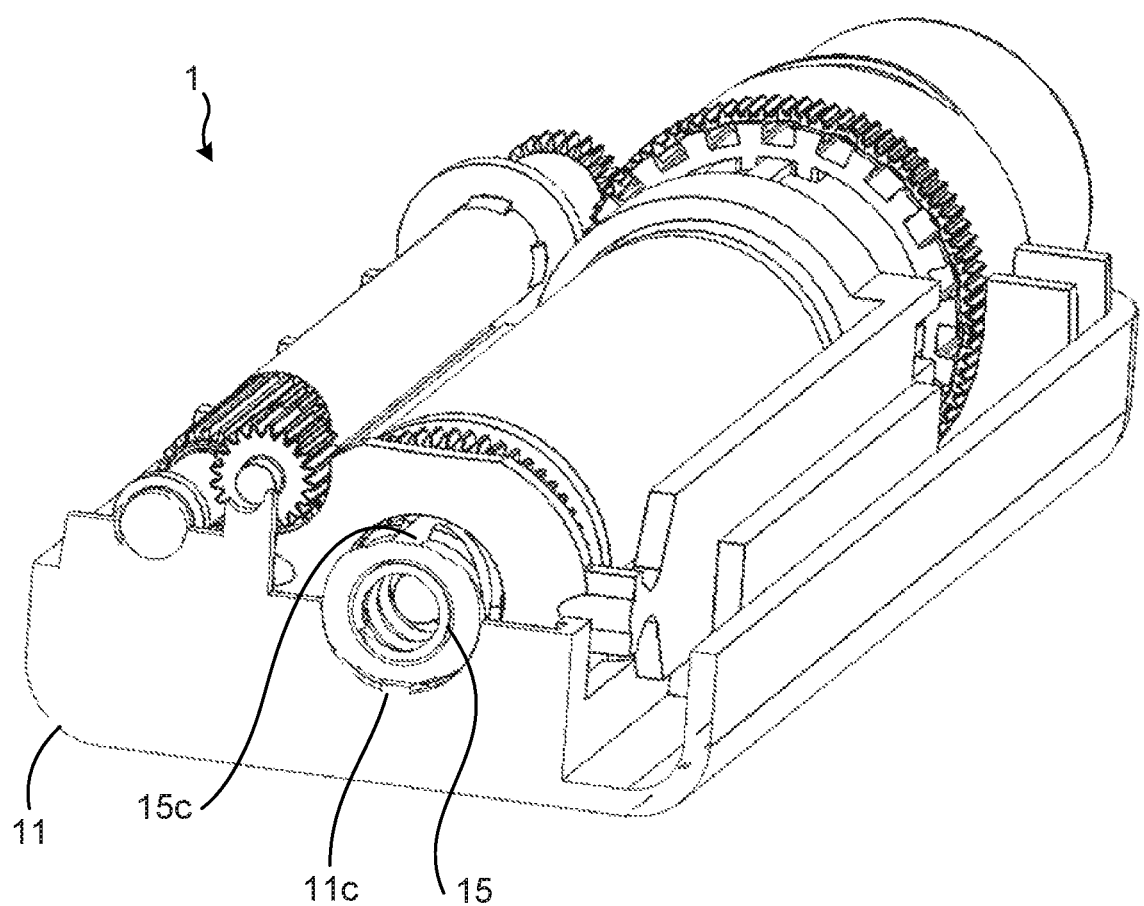
FIG. 6 is a perspective view the medicament delivery device in FIG. 5 showing another cross section.

The plunger rod 15 is rotationally fixed to the body 11. The plunger rod 15 may for example have one or more axial grooves 15c and the body 11 may be provided with one or more corresponding protrusions extending into the axial groove(s) 15c, as shown in FIG. 6. The plunger rod 15 may furthermore be hollow and the first biasing member 17 may be received by the plunger rod 15, axially biasing the plunger rod 15 towards the proximal end 1a of the medicament delivery device 1. The guide rod 19 is received by the first biasing member 17 and is arranged to maintain the first biasing member 17 in the correct position.

Figures 4C, 4D, 4E:
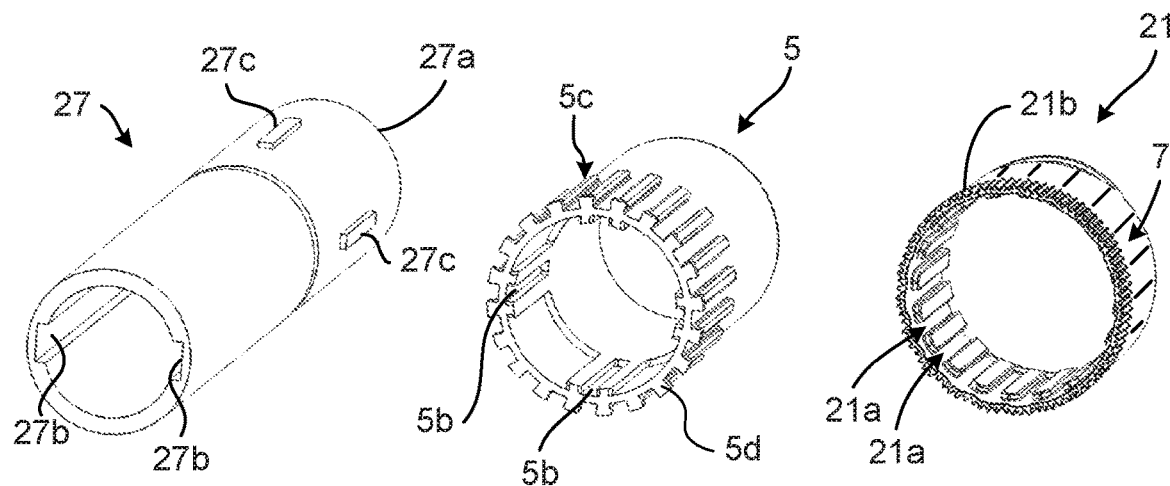
FIG. 4c is a perspective view of an example of a dose setting tube.
FIG. 4d is a perspective view of an example of an activation member.
FIG. 4e is a perspective view of tubular medicament scale member.
Figure 5:
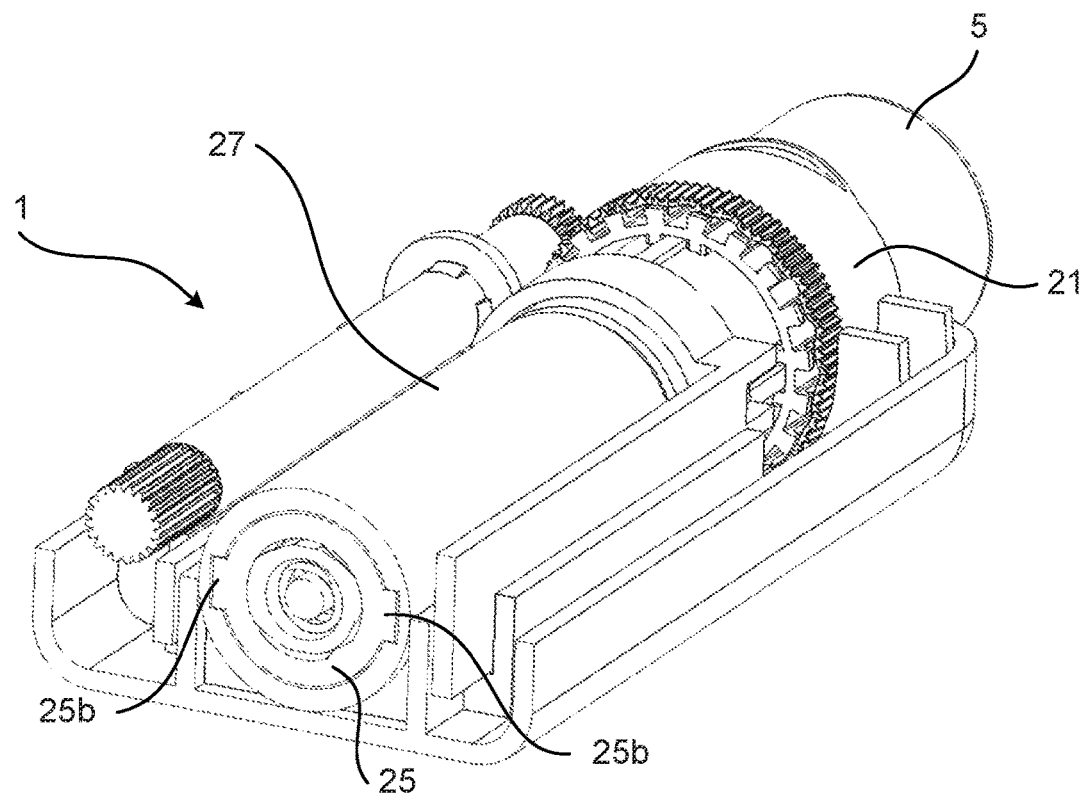
FIG. 5 is a perspective view of the medicament delivery device in FIG. 3 showing a cross section thereof.

The internal components of the medicament delivery device 1 will now be described in more detail with reference to FIGS. 3 to 4e. As shown in FIG. 3 the plunger rod 15 is provided with a first external thread 15a. The stop nut 23 is provided with an internal thread 23a, as shown in FIG. 4b. The stop nut 23 is threaded in a first direction. The stop nut 23 receives the plunger rod 15, and the internal thread 23a of the stop nut 23 engages with the first external thread 15a of the plunger rod 15.

The plunger rod 15 is provided with a second external thread 15b. The first external thread 15a and the second external thread 15b define double helix threads. The dose setting nut 25 is provided with an internal thread 25a, as shown in FIG. 4a. The dose setting nut 25 is threaded in a second direction which is opposite to the first direction. One of the stop nut 23 and the dose setting nut 25 may have a left-hand thread and the other may have a right-hand thread. The dose setting nut 25 receives the plunger rod 15, and the internal thread 25a of the dose setting nut 25 engages with the second external thread 15b of the plunger rod 15.

The dose setting nut 25 is arranged between the stop nut 23 and a distal end 15d of the plunger rod 15. The dose setting nut 25 is in particular received by the dose setting tube 27 and arranged between the stop nut 23 and a distal end wall 27a of the dose setting tube 27. The dose setting nut 25 is rotatably fixedly engaged to the dose setting tube 27 but is slidably arranged relative to the dose setting tube 27. The dose setting nut 25 is rotatably fixedly engaged with the dose setting tube 27 to prevent relative rotation between the dose setting nut 25 and the dose setting tube 27, an example of implementation of this being shown in FIG. 5. Rotation of the dose setting tube 27 hence results in rotation of the dose setting nut 25 around the plunger rod 15. This enables axial displacement of the dose setting nut 25 relative to the plunger rod 15. This functionality of the dose setting nut 25 and the placement of the stop nut 23 provides for a dose setting functionality as will be described in the following.

Figure 7:
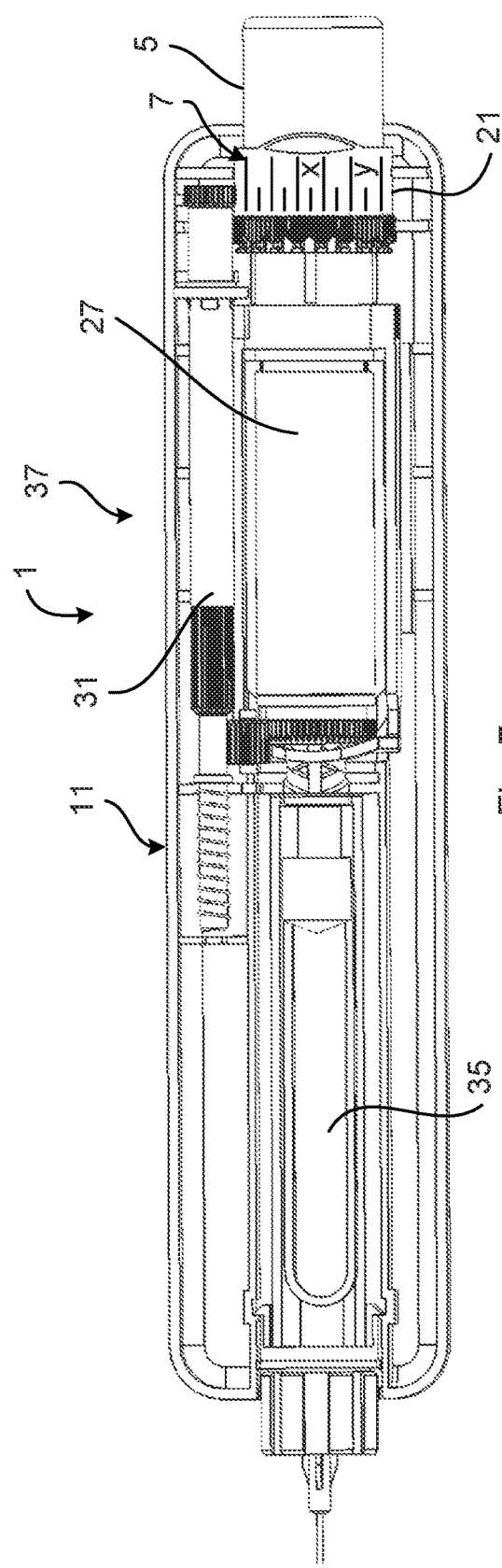
FIG. 7 shows a side view of the medicament delivery device in FIG. 2, with one half of the body or housing removed, prior to activation.
Figure 8:
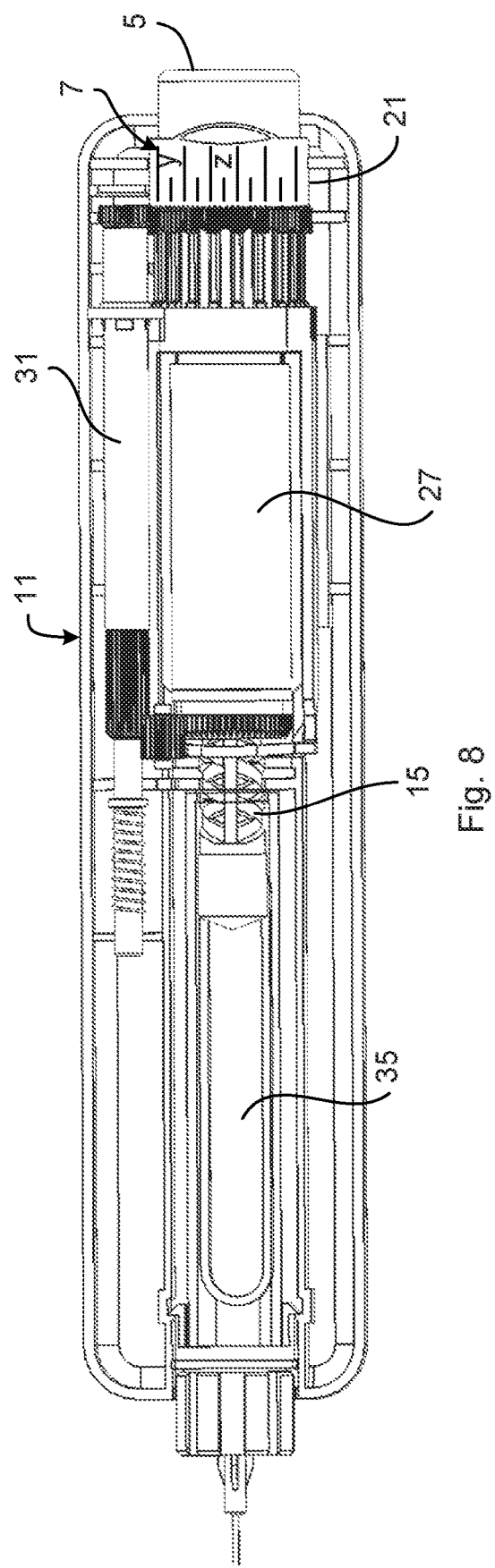
FIG. 8 shows a side view of the medicament delivery device in FIG. 7 post activation.

The tubular medicament scale member 21 receives the activation member 5, and the activation member 5 receives the dose setting tube 27. The activation member 5 is axially movable between a start position, as shown in FIG. 7, and an end position, as shown in FIG. 8.

In the start position, the activation member 5 is rotatably fixedly engaged with the tubular medicament scale member 21 to prevent relative rotation between them. The activation member 5 is however movable in the axial direction relative to the tubular medicament scale member 21. Moreover, the activation member 5 is rotatably fixedly engaged with the dose setting tube 27 when the activation member 5 is in the start position to prevent relative rotation between them. Thus, when the activation member 5 is rotated in the start position, the dose setting tube 27 and the dose setting nut 25 both rotate concurrently with the activation member 5. The dose setting nut 25 is thereby screwed along the plunger rod 15, whereby the axial distance between the dose setting nut 25 and the stop nut 23 may be adjusted, because when the activation member 5 is rotated in the start position, the stop nut 23 is prevented from rotation by the lock member 29. This axial distance between the dose setting nut 25 and the stop nut 23 defines the amount of the dose that can be given by the medicament delivery device 1. The larger the distance, the larger is the dose. Furthermore, due to the rotation of the tubular medicament scale member 21 the dose can visually be read from the visual medicament dose scale 7.

According to one variation, the rotational engagement of the dose setting tube 27 and the dose setting nut 25 may be obtained by the dose setting tube 27 being provided with internal axial grooves 27b, as shown in FIG. 4c, and the dose setting nut 25 may be provided with corresponding lugs 25b arranged to engage with the internal axial grooves 27b of the dose setting tube 27.

According to one variation, the dose setting tube 27 may have external axial ribs 27c and the activation member 5 may have corresponding inner axial grooves 5b for receiving the external axial ribs 27c, to thereby obtain rotational engagement between the dose setting tube 27 and the activation member 5.

According to one variation, the activation member 5 comprises a plurality of external axial ribs 5c that extend only along a portion of the longitudinal extension of the activation member 5. The tubular medicament scale member 21 may have corresponding internal axial grooves 21a arranged to engage with the external axial ribs 5c of the activation member 5. Due to the axial length of the external axial ribs 5c being shorter than the axial length of the activation member 5, the tubular medicament scale member 21 may be released from the activation member 5 when the activation member 5 is moved towards its end position. The tubular medicament scale member 21 may thereby be released to freely rotate relative to the activation member 5.

The functionality of the gear train arrangement 37 will now be described in more detail. The gear train arrangement 37 is operable between a decoupled state and a coupled state. In FIG. 3, the gear train arrangement 37 is shown in the decoupled state, while in FIG. 8, the gear train arrangement 37 is shown in the coupled state. In the decoupled state the gear train arrangement 37 decouples the stop nut 23 from the tubular medicament scale member 21. In the coupled state the gear train arrangement 37 couples the stop nut 23 to the tubular medicament scale member 21 in order to be able to transfer rotational motion of the stop nut 23 to the tubular medicament scale member 21. A measure of axial movement of the plunger rod 15 may thus be conveyed to the tubular medicament scale member 21. Thereby an indication may be provided, on the visual medicament dose scale 7, of an amount of expelled medicament from the medicament container 35. In particular, the visual medicament dose scale 7 shows the amount of the dose that is left to be delivered.

According to the present example, the scale rotation axle 31 is arranged parallel to the plunger rod 15. The scale rotation axle 31 is arranged to transfer rotational motion of the stop nut 23 to the tubular medicament scale member 21. The scale rotation axle 31 thus extends axially from the stop nut 23 to the tubular medicament scale member 21.

The stop nut 23 has a plurality of external stop nut teeth 23b extending along its periphery. The intermediate wheel 33 has intermediate wheel teeth 33a engaging with the stop nut teeth 23b. The tubular medicament scale member 21 has a plurality of scale member teeth 21b extending along its periphery. The scale rotation axle 31 has a plurality of first scale rotation axle teeth 31a engageable with the scale member teeth 21b. The scale rotation axle 31 has a plurality of second scale rotation axle teeth 31b engageable with the intermediate wheel teeth 33a of the intermediate wheel 33.

The scale rotation axle 31 is furthermore biased towards the distal end 1b of the medicament delivery device 1, i.e. such that in the default position of the scale rotation axle 31 the gear train arrangement 37 is in the decoupled state. In this position of the scale rotation axle 31, the first scale rotation axle teeth 31a are axially offset from the scale member teeth 21b and the second scale rotation axle teeth 31b are axially offset from the intermediate wheel teeth 33a. The activation member 5 is arranged to axially displace the scale rotation axle 31 to enable a coupling between the stop nut 23 and the tubular medicament dose scale member 21. The scale rotation axle 31 may therefore be provided with a flange 31c which is arranged to be set in physical contact with the proximal end 5d of the activation member 5 when the activation member 5 is moved from the start position towards the end position. When the proximal end 5d of the activation member bears against the flange 31c the scale rotation axle 31 may be moved axially towards the proximal end 1a of the medicament delivery device 1. The axial offset may thereby be eliminated and the scale member teeth 21b may engage with the first scale rotation axle teeth 31a and the intermediate wheel teeth 33a may engage with the second scale rotation axle teeth 31b. The gear train arrangement 37 is thereby set in the coupled state.

The lock member 29 is in a first state, corresponding to the decoupled state of the gear train arrangement 37, arranged to prevent rotation of the stop nut 23 relative to the plunger rod 15. In a second state, corresponding to the coupled state of the gear train arrangement 37, the lock member 29 is arranged to enable rotation of the stop nut 23 relative to the plunger rod 15. During the above-described rotation of the activation member 5, the lock member 29 is in the first state preventing rotation of the stop nut 23. Thereby the axial biasing of the plunger rod 15 may be maintained.

The lock member 29 may for example include a spring washer which receives the plunger rod 15. The spring washer may be arranged at a proximal side of the stop nut 23. The lock member 29 may furthermore include a release arm 29a which in a default state maintains the tension in the spring washer such that it bears against the stop nut 23. This occurs when the activation member 5 is in the start position.

When the activation member 5 is moved towards the end position, the proximal end 5d of the activation member 5 pushes the release arm 29a towards the proximal end 1a of the medicament delivery device 1. The tension in the spring washer may thereby be reduced and the lock member 29 may obtain its second state, enabling rotation of the stop nut 23.

In FIG. 7, the gear train arrangement 37 is shown in the decoupled state. According to the example in FIG. 7, although the pointer or indicator is not shown, the dose is set to x volume units. Furthermore, according to the example, a lower volume unit y is also shown on the visual medicament dose scale 7. In FIG. 8, the gear train arrangement 37 is shown in the coupled state. In the coupled state, the stop nut 23 is able to rotate. Due to the stop nut 23 now being able to rotate the axially biased plunger rod 15 is allowed to move axially, wherein the dose setting nut 25 slides axially relative the dose setting tube 27, concurrently with the plunger rod 15. The plunger rod 15 may thus move further into the medicament container 35 to thereby expel a medicament therefrom. The rotation of the stop nut 23 is transferred by means of the scale rotation axle 31 to the tubular medicament scale member 21, which in turn is rotated maximum one turn, corresponding to the axial displacement of the plunger rod 15. In this manner, the amount of medicament remaining of the set dose may at any instance of drug administration be visually monitored by means of the visual medicament dose scale 7. According to the present example, the tubular medicament scale member 21, and thus the visual medicament dose scale 7, has been rotated in a direction upwards in the figure and the set dose x has been partially delivered, such that the remaining dose is z volume units, z being a smaller quantity than y.

The medicament delivery device may in particular be of disposable multi-dose type.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A medicament delivery device comprising:
   a body,
   an axially biased plunger rod provided with a first external thread,
   an activation member arranged to activate the plunger rod,
   a tubular medicament scale member receiving the activation member, which tubular medicament scale member is rotatable relative to the body and provided with a visual medicament dose scale,
   a stop nut which receives the plunger rod and which stop nut is provided with an internal thread engaging with the first external thread of the plunger rod, and
   a gear train arrangement arranged to, in a decoupled state decouple the stop nut from the tubular medicament scale member, and in a coupled state couple the stop nut to the tubular medicament scale member for transferring rotational motion of the stop nut to the tubular medicament scale member, in order to convey a measure of axial movement of the plunger rod to the tubular medicament scale member, thereby providing an indication, on the visual medicament dose scale, of an amount of expelled medicament.

2. The medicament delivery device as claimed in claim 1, wherein the gear train arrangement includes a scale rotation axle arranged parallel to the plunger rod, wherein the scale rotation axle is arranged to transfer rotational motion of the stop nut to the tubular medicament scale member.

3. The medicament delivery device as claimed in claim 2, wherein the scale rotation axle has a plurality of first scale rotation axle teeth engageable with scale member teeth of the tubular medicament scale member.

4. The medicament delivery device as claimed in claim 1, wherein the gear train arrangement comprises an intermediate wheel having intermediate wheel teeth engaging with stop nut teeth of the stop nut.

5. The medicament delivery device as claimed in claim 2, wherein the scale rotation axle has a plurality of second scale rotation axle teeth engageable with the intermediate wheel teeth of the intermediate wheel.

6. The medicament delivery device as claimed in claim 2, wherein the activation member is arranged to axially displace the scale rotation axle to enable the coupling between the stop nut and the tubular medicament dose scale member.

7. The medicament delivery device as claimed in claim 1, comprising a dose setting tube receiving the plunger rod, wherein the dose setting tube is rotatably fixed to the activation member to prevent relative rotation between the dose setting tube and the activation member.

8. The medicament delivery device as claimed in claim 7, comprising a dose setting nut receiving the plunger rod inside the dose setting tube, which dose setting nut is arranged between the stop nut and a distal end wall of the dose setting tube, wherein the internal thread of the stop nut is threaded in a first direction and the dose setting nut is provided with an internal thread threaded in a second direction, which plunger rod has a second external thread and wherein the internal thread of the dose setting nut engages with the second external thread of the plunger rod, and which dose setting nut is rotatably fixed relative to the dose setting tube.

9. The medicament delivery device as claimed in claim 8, wherein the first external thread and the second external thread of the plunger rod define double helix threads.

10. The medicament delivery device as claimed in claim 1, comprising a lock member which in a first state, corresponding to the decoupled state of the gear train arrangement, is arranged to prevent rotation of the stop nut relative to the plunger rod and in a second state, corresponding to the coupled state of the gear train arrangement, is arranged to enable rotation of the stop nut relative to the plunger rod.

11. The medicament delivery device as claimed in claim 10, wherein the activation member is arranged to actuate the lock member from the first state to the second state.

12. The medicament delivery device as claimed in claim 1, wherein the plunger rod is rotatably fixed relative to the body.

13. The medicament delivery device as claimed in claim 1, wherein the activation member is movable between a start position and an end position, wherein the activation member is rotatably fixedly engaged with the tubular medicament scale member in the start position.

14. The medicament delivery device as claimed in claim 13, wherein the activation member is released from the rotatably fixed engagement with the tubular medicament scale member in the end position.

15. The medicament delivery device as claimed in claim 12, wherein in the start position rotation of the activation member provides rotation of the dose setting nut and of the dose setting tube relative to the plunger rod, thereby setting an axial distance between the stop nut and the dose setting nut, wherein the amount of rotation of the activation member provides a measure of a medicament dose amount indicated on the visual medicament dose scale.

16. A medicament delivery device comprising:
a body;
an axially biased plunger rod provided with a first external thread;
an activation member arranged to activate the plunger rod;
a tubular medicament scale member receiving the activation member, which tubular medicament scale member is rotatable relative to the body and provided with a visual medicament dose scale;
a stop nut which receives the plunger rod and which stop nut is provided with an internal thread engaging with the first external thread of the plunger rod; and
a gear train arrangement arranged offset and parallel to the plunger rod.

17. The medicament delivery device of claim 16 wherein the gear train arrangement includes a scale rotation axle arranged parallel to the plunger rod that transfers rotational motion of the stop nut to the tubular medicament scale member.

18. The medicament delivery device of claim 16 where the gear train arrangement has a coupled state and a decoupled state, where in the decoupled state the stop nut is decoupled from the tubular medicament scale member, and in a coupled state the stop nut is coupled to the tubular medicament scale member for transferring rotational motion of the stop nut to the tubular medicament scale member to convey a measure of axial movement of the plunger rod to the tubular medicament scale member.

19. The medicament delivery device of claim 18 where the measure of axial movement is indicated on the visual medicament dose scale and represents an amount of expelled medicament.

20. The medicament delivery device of claim 16 further comprising a dose setting tube that receives the plunger rod, where the dose setting tube is rotatably fixed to the activation member to prevent relative rotation between the dose setting tube and the activation member.

* * * * *